United States Patent
Aboul-Hosn et al.

[11] Patent Number: 6,152,704
[45] Date of Patent: Nov. 28, 2000

[54] BLOOD PUMP WITH TURBINE DRIVE

[75] Inventors: Walid Najib Aboul-Hosn, Sacramento; Kelly McCrystle, Healdsburg, both of Calif.; Desmond O'Connell, Seattle, Wash.

[73] Assignee: A-Med Systems, Inc., West Sacramento, Calif.

[21] Appl. No.: 09/164,396

[22] Filed: Sep. 30, 1998

[51] Int. Cl.[7] .................................................. F04B 17/00
[52] U.S. Cl. ...................... 417/360; 417/405; 418/415.1; 604/151
[58] Field of Search ................................... 417/360, 420, 417/405; 600/16, 17; 623/3; 604/131, 151, 500; 415/213.1, 214.1

[56] References Cited

U.S. PATENT DOCUMENTS

| | | | |
|---|---|---|---|
| 3,373,927 | 3/1968 | Miller | 417/405 |
| 4,135,253 | 1/1979 | Reich et al. . | |
| 4,606,698 | 8/1986 | Clausen et al. | 417/360 |
| 4,625,712 | 12/1986 | Wampler . | |
| 4,846,152 | 7/1989 | Wampler et al. . | |
| 4,895,557 | 1/1990 | Moise et al. . | |
| 4,898,518 | 2/1990 | Hubbard et al. . | |
| 4,984,972 | 1/1991 | Clausen et al. . | |
| 5,145,333 | 9/1992 | Smith | 417/405 |
| 5,147,186 | 9/1992 | Buckholtz . | |
| 5,539,503 | 7/1996 | Johnson . | |
| 5,580,216 | 12/1996 | Munch . | |
| 5,741,234 | 4/1998 | Aboul-Hosn . | |
| 5,746,709 | 5/1998 | Rom et al. . | |
| 5,782,634 | 7/1998 | Lingenhöle et al. . | |

FOREIGN PATENT DOCUMENTS

WO 94/17304  8/1994  WIPO .

OTHER PUBLICATIONS

Brochure for 3M™ Sarns™ Centrifugal System, No Date Available.

Brochure for 3M™ Sarns and DCI Health Care Cardiovascular System Products, No Date Available.

Primary Examiner—Charles G. Freay
Attorney, Agent, or Firm—Jonathan Spangler

[57] ABSTRACT

A blood pump for use in CPB and other heart surgeries includes a sterilizable blood pump removably attached to a turbine drive unit. An impeller within the fully enclosed and sterile blood pump moves the blood from the pump inlet to the pump outlet. The pump snaps onto the turbine drive unit and a magnetic coupling between the pump and the drive unit is used to transmit the rotation of a turbine shaft to the pump impeller. The turbine drive unit is preferably a sterilizable unit which may be placed directly in the sterile surgical field. The blood pump with turbine drive allows the blood pump to be placed close to the surgical site and minimizes the length of the tubing required for connecting the pump to the patient.

9 Claims, 3 Drawing Sheets

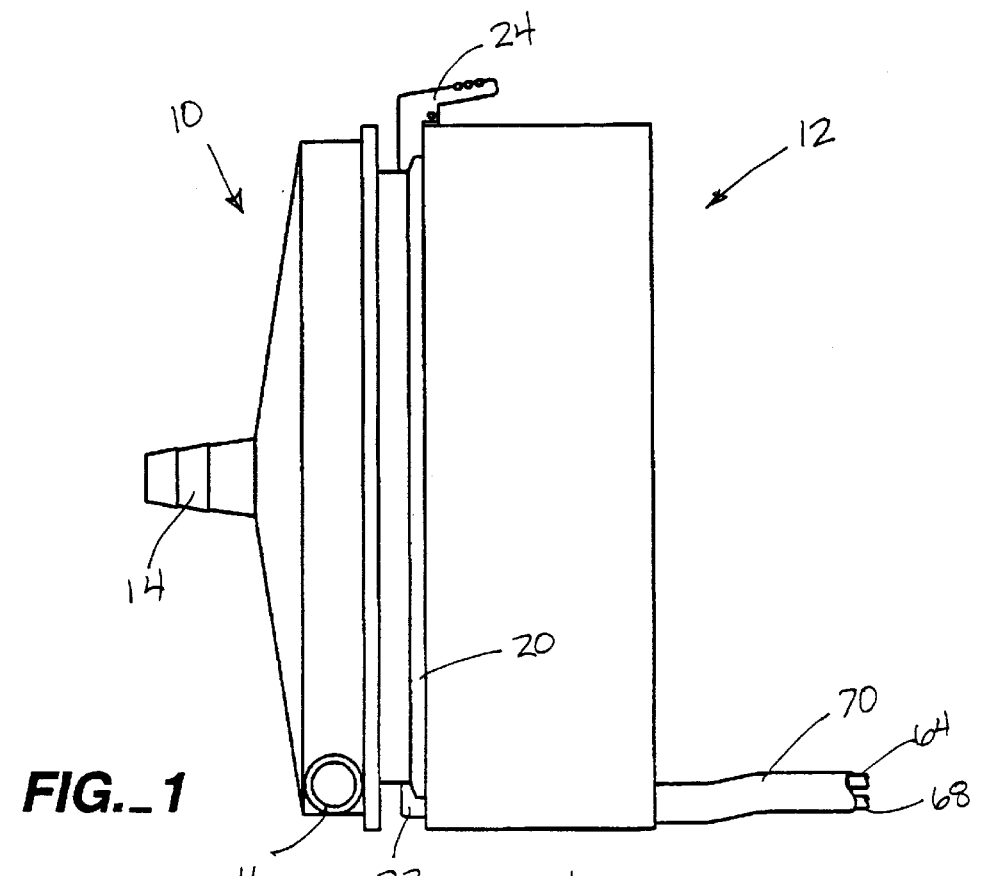
FIG._1
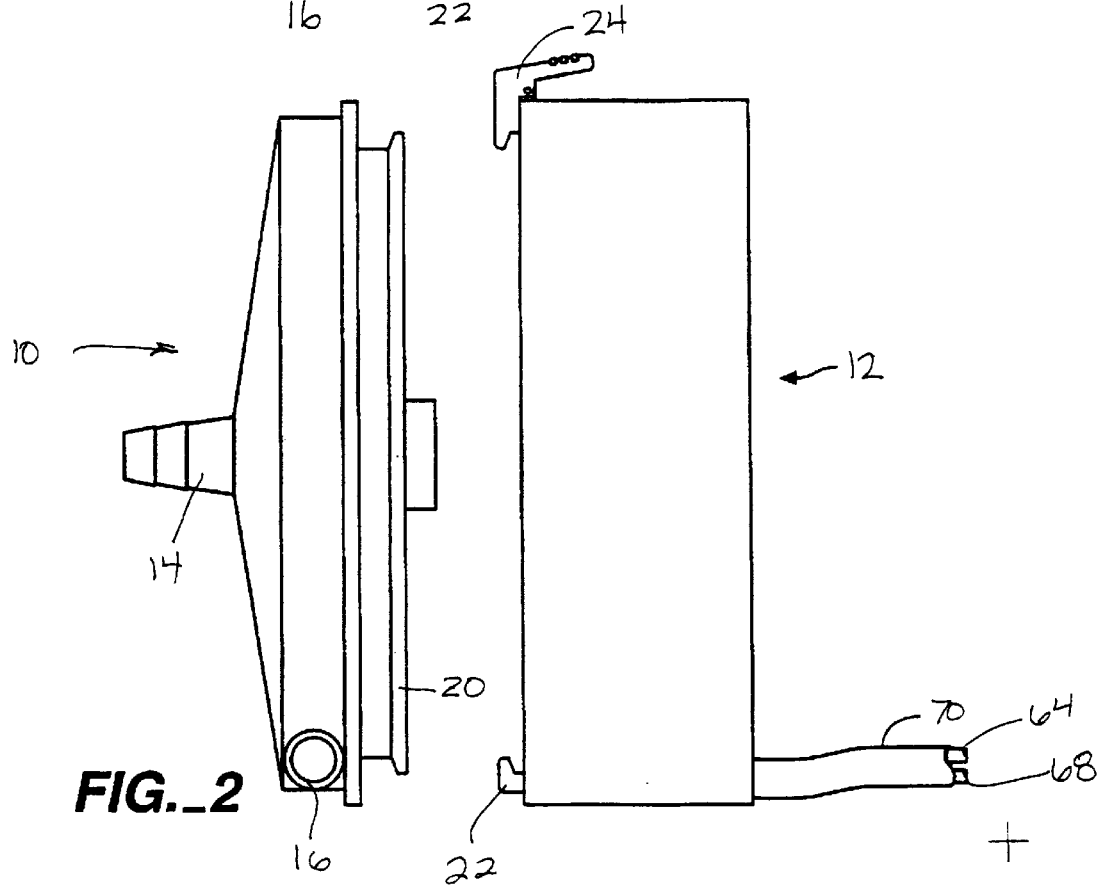
FIG._2

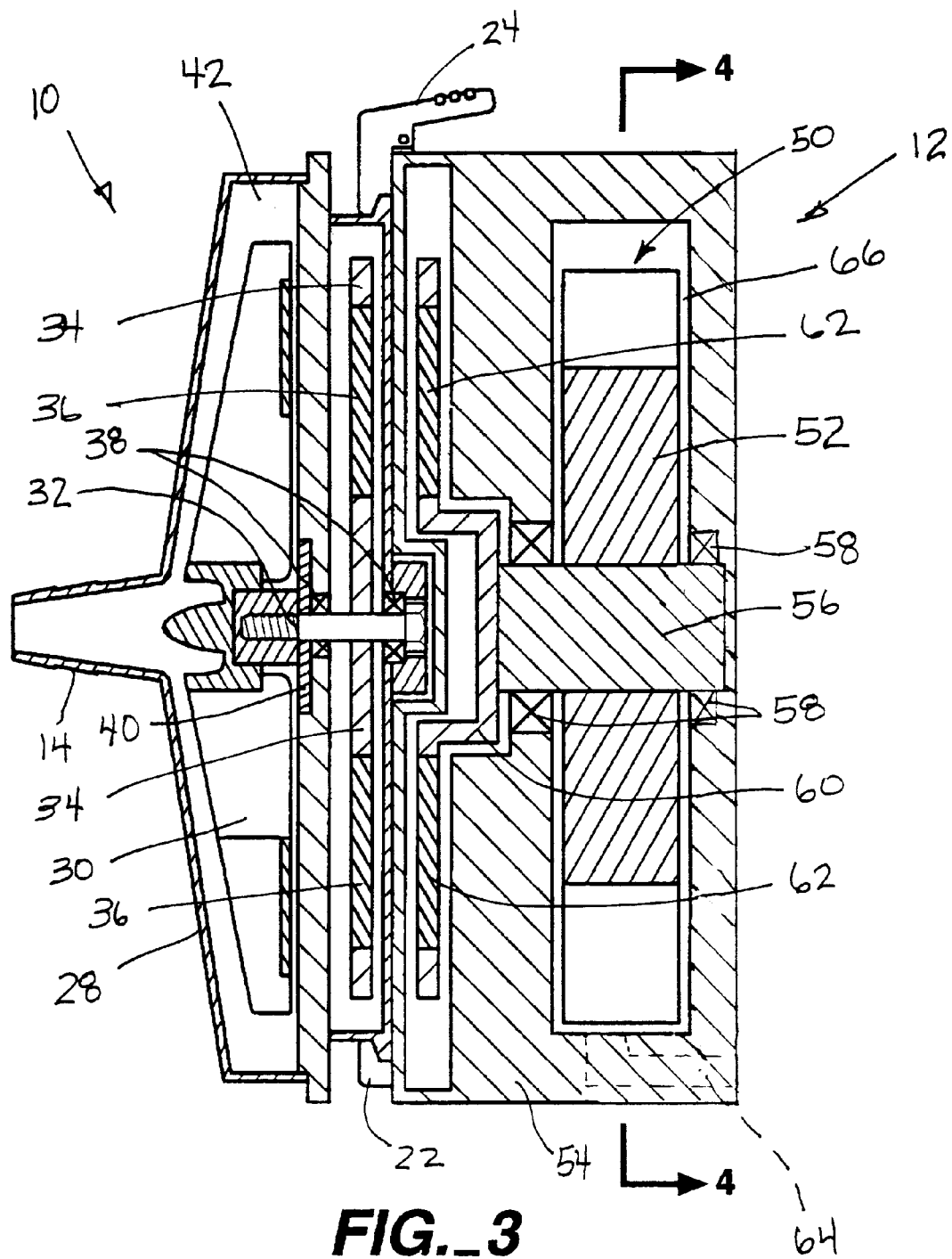
FIG._3

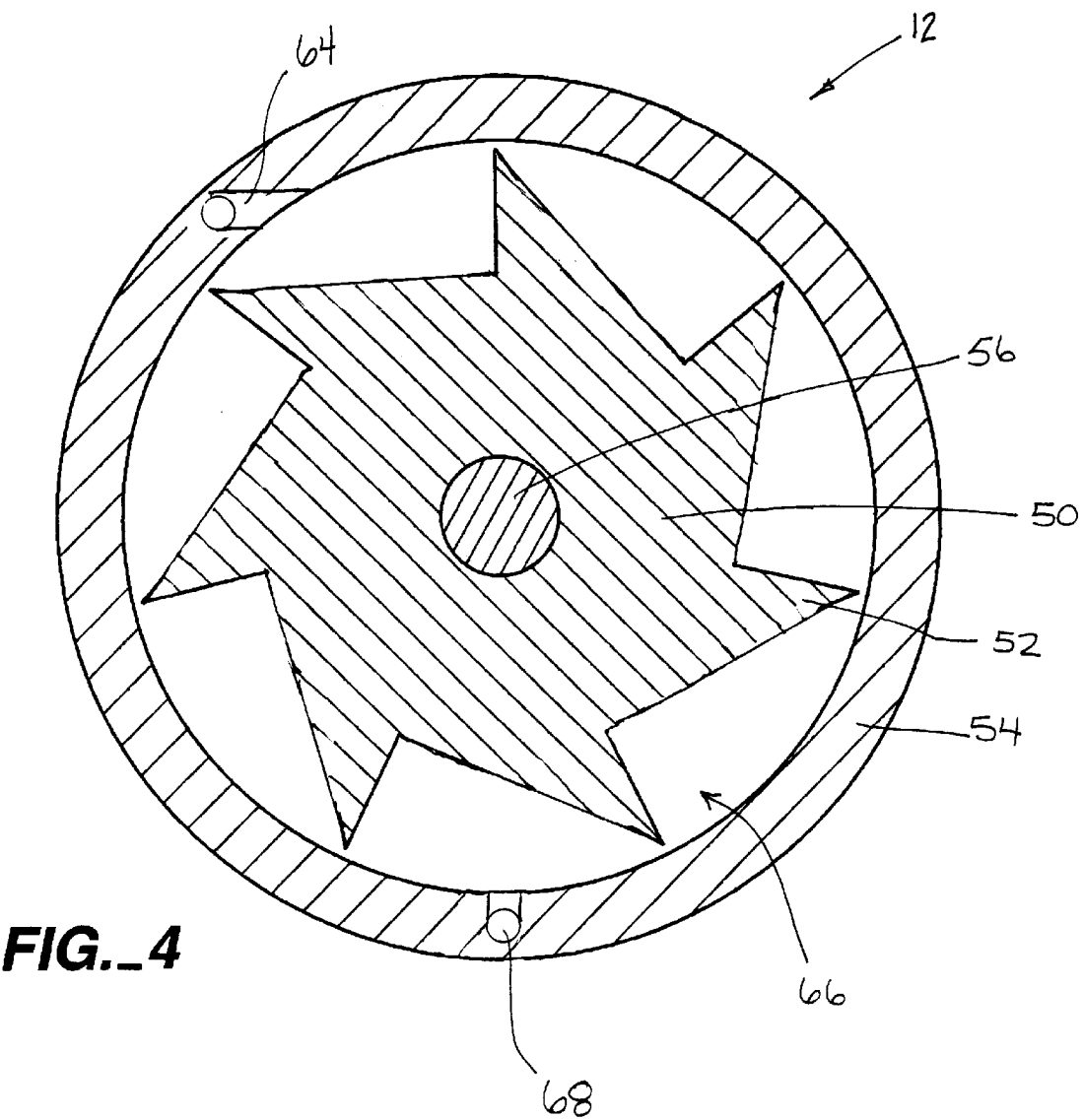
FIG._4

BLOOD PUMP WITH TURBINE DRIVE

BACKGROUND OF THE INVENTION

1. Field of the Invention

The invention relates to a blood pump, and more particularly, the invention relates to a centrifugal blood pump system with a turbine drive assembly.

2. Brief Description of the Related Art

Blood pumps used in surgical procedures such as cardiopulmonary bypass (CPB) and coronary artery bypass grafting (CABG) are single-use devices. These blood pumps are generally powered by a reusable electric motor which drives the pump through a magnetic coupling. However, the reusable electric motors are not sterilizable. Thus, the motor and attached pump are positioned outside the sterile surgical field at a location away from the patient. The disposable pump is connected to the patient by long lengths of tubing which transport the patient's blood to and from the blood pump. The long lengths of tubing increase the priming volume of the pump which is the amount of the patient's blood and/or saline which must be drawn into the tubing and the pump to prime the pump before blood begins to be returned to the patient.

Long lengths of tubing connecting the pump to the patient also increase the amount of foreign material which comes into contact with the patient's blood, increasing trauma to the patient. A typical CPB circuit includes several feet of flexible tubing that the patient's blood flows through. In order to prevent blood clots, the patient's blood is generally treated with Heparin. The use of Heparin is preferably minimized because Heparin prevents the blood from clotting.

In either stopped heart or beating heart surgery, it is desirable to minimize the priming volume of the blood pump by placing the pump as close as possible to the surgical site. By placing the pump closer to the surgical field, the amount of saline required to prime the bypass circuit is reduced which reduces the likelihood that a transfusion will be required. Previous attempts to move the blood pump closer to the patient have involved the use of a cable drive for the blood pump which allows the sterile pump to be located within the sterile surgical field while being driven from a remotely located motor. However, the cable used in the cable drive system may break causing pump failure.

Accordingly, it would be desirable to provide a blood pump system which allows the blood pump to be positioned within the surgical field close to the surgical site to minimize the priming volume of the pump. In addition, it would be desirable to drive a blood pump in a manner which does not generate heat as in a system using an electric motor.

SUMMARY OF THE INVENTION

The present invention relates to a blood pump system including a centrifugal blood pump having an impeller, an impeller drive shaft, and a magnetic coupling connected to the drive shaft. A turbine unit is removably connected to the blood pump. The turbine unit includes a turbine wheel connected to a magnetic coupling for driving the centrifugal blood pump. A compressed air supply line is connected to the turbine unit for driving the turbine wheel.

In accordance with an additional aspect of the present invention, a blood pump system includes a disposable centrifugal blood pump having a magnetic coupling and a hermetically sealed pump housing. A turbine unit is removably connected to the blood pump by the magnetic coupling. The turbine unit also has a hermetically sealed housing.

The blood pump with sterilizable turbine drive allows the blood pump to be placed close to the surgical site minimizing the length of the tubing required for connecting the pump to the patient.

In addition, the turbine drive unit provides advantages over cable drive systems and electric motor driven blood pumps in that there is no cable which may break and there is no heat generation by the turbine drive.

BRIEF DESCRIPTION OF THE DRAWINGS

The invention will now be described in greater detail with reference to a preferred embodiment illustrated in the accompanying drawings, in which like elements bear like reference numerals, and wherein:

FIG. 1 is a side view of a blood pump connected to a turbine drive unit according to the present invention;

FIG. 2 is an exploded side view of the blood pump disconnected from the turbine drive unit;

FIG. 3 is a side cross sectional view of the blood pump and turbine drive unit of FIGS. 1 and 2; and FIG. 4 is a cross sectional view of the turbine taken along line 4—4 of FIG. 3.

DETAILED DESCRIPTION OF THE PREFERRED EMBODIMENT

A blood pump system according to the present invention as illustrated in FIGS. 1 and 2 includes a sterilizable blood pump 10 removably attached to a sterilizable turbine drive unit 12. The blood pump 10 has an axial blood inlet 14 and a tangential blood outlet 16. An impeller (not shown) within the fully enclosed and sterile blood pump 10 moves the blood from the inlet 14 to the outlet 16. The pump 10 snaps onto the turbine drive unit 12 and a magnetic coupling between the pump 10 and the drive unit 12 is used to transmit the rotation of a turbine shaft (not shown) to the pump impeller. After use, the pump 10 is removed from the sterilized turbine drive unit 12 and replaced with a new sterile blood pump for the next patient.

The blood pump 10 includes an annular flange 20 which is configured to be received on the turbine drive unit 12 and is used to retain the blood pump connected to the drive unit. A fixed L-shaped tab 22 and a movable lever arm 24 of the turbine unit 12 engage the annular flange 20 of the blood pump and secure the blood pump in place as illustrated in FIG. 1.

As shown in FIG. 3, the blood pump includes a housing 28 containing an impeller 30 which is rotatably mounted in the housing. The impeller 30 is connected to an impeller drive shaft 32. Also connected to the impeller drive shaft 32 is a disk shaped member 34 containing a plurality of magnets 36. The impeller drive shaft 32 is rotatably mounted in the housing 28 by two sets of bearings 38. The disk shaped member 34 and magnets 36 provide one half of the magnetic coupling for transmitting rotation from the turbine drive unit 12 to the blood pump 10. A sealing member 40 is provided around the impeller drive shaft 32 to seal the impeller chamber 42 from the bearing assembly. Impeller chamber 42 is hermetically sealed to annular flange 20, such as by adhesive, sonic welding, or the like.

The turbine drive unit 12 as illustrated in FIG. 3 includes a rotatable turbine wheel 50 having a plurality of wedged shaped fins 52 shown most clearly in FIG. 4. The wedge shaped fins 52 may be replaced by any other known configuration for a turbine wheel and the number and configuration of the fins 52 may be varied to maximize efficiency.

The turbine wheel 50 is rotatable in a housing 54 of the turbine drive unit 12 by a rotatable turbine shaft 56 mounted in two sets of bearings 58. Also connected to the rotatable turbine shaft 56 is a disk shaped member 60 having a plurality of magnets 62 mounted therein. When the blood pump 10 is mounted on the turbine drive unit 12, the disk shaped member 34 of the blood pump is directly opposed to the disk shaped member 60 of the turbine drive unit 12. Accordingly, rotation of the turbine drive unit 12 causes corresponding rotation of the blood pump impeller 30.

The turbine drive unit 12 is driven by the compressed air supply or other fluid supply which is delivered through a supply line 64. The supply line enters the turbine chamber 66 at an angle with respect to the radius of the turbine wheel 50 as shown in FIG. 4. Air or other fluid exits the turbine chamber 66 through the discharge line 68. As illustrated in FIGS. 1 and 2 the supply line 64 and the discharge line 68 may be contained within a single sheath 70.

According to one preferred embodiment of the present invention, the turbine drive unit 12 is sterilizable so that the sterile blood pump 10 may be connected to the turbine drive unit 12 and the entire system may be placed within the sterile surgical field. The turbine drive unit 12 may be sterilizable, such as by an autoclave, ETO, radiation, or the like, or may be a disposable single use device. The turbine chamber 66 is hermetically sealed such that the compressed air or other fluid which drives the turbine wheel 50 is not delivered to the sterile surgical field.

Although the present invention has been illustrated with a magnetic coupling between the blood pump 10 and the turbine drive unit 12, it should be understood that other types of couplings such as a mechanical coupling may also be used without departing from the present invention. In addition, the blood pump 10 and turbine drive unit 12 may be incorporated in a single disposable device.

Monitoring of the operation of the blood pump 10 may be performed by providing sensors, such as a retro-reflective tachometer using fiber optic light, in the turbine drive unit 12 or the blood pump which deliver information regarding the rotation of the turbine wheel 50 and the blood pump impeller 30 to a controller.

While the invention has been described in detail with reference to the preferred embodiments thereof, it will be apparent to one skilled in the art that various changes and modifications can be made and equivalents employed, without departing from the present invention.

What is claimed is:

1. A blood pump system, comprising:

a sterilizable centrifugal blood pump having a pump housing, an impeller disposed within a first chamber of the pump housing, an impeller drive shaft coupled to the impeller and extending into a second chamber of the pump housing, and a magnetic coupling connected to the drive shaft and disposed within the second chamber of the pump housing, the pump housing including an annular ridge formed about the periphery of the second chamber;

a sterilizable turbine unit having a turbine housing, a turbine wheel dispose within a first chamber of the turbine housing, a turbine drive shaft coupled to the turbine wheel and extending into a second chamber of the turbine housing, a magnetic coupling connected to the turbine drive shaft and disposed within the second chamber of the turbine housing, a tab member disposed along the periphery of the second chamber of the turbine housing for engagement with at least a portion of the annular ridge of the pump housing, and a lever member hingedly disposed along the periphery of the second chamber of the turbine housing for selective engagement with at least a portion of the annular ridge of the pump housing such that the centrifugal blood pump and turbine unit may be removably coupled together and positioned within the sterile surgical field; and a pressurized fluid supply line in fluid communication with the first chamber of the turbine housing for driving the turbine wheel to thereby drive the centrifugal blood pump when removably coupled to the turbine unit.

2. The blood pump system of claim 1, wherein the magnetic coupling of the blood pump includes a rotatable disk fixed to the impeller drive shaft and a plurality of magnets in the disk.

3. The blood pump system of claim 2, wherein the magnetic coupling of the turbine drive unit includes a rotatable disk fixed to a turbine drive shaft and a plurality of magnets in the disk.

4. The blood pump system of claim 1, wherein the blood pump is a sterile disposable unit.

5. The blood pump system of claim 1, wherein the compressed air supply line directs the compressed air into the first chamber of the turbine housing at an angle with respect to a radius of the turbine wheel.

6. The blood pump system of claim 1, further comprising an air discharge line connected to the first chamber of the turbine housing.

7. A blood pump system, comprising:

a sterilizable centrifugal blood pump including a pump housing having an internally disposed pump assembly, the pump housing including a first chamber having a fluid inlet and outlet, a second chamber sealed from the first chamber, and an annular ridge formed about the periphery of the second chamber, the pump assembly including an impeller rotatably disposed within the first chamber, a magnetic coupling rotatably disposed within the second chamber, and a drive shaft extending between the magnetic coupling and the impeller; and a sterilizable turbine unit including a turbine housing with an internally disposed turbine assembly, the turbine housing including a first chamber having a fluid inlet and fluid outlet, a second chamber rotatably receiving a magnetic coupling and being sealed from the first chamber, and a coupling assembly including a tab member and a lever member which cooperate to engage the annular ridge of the pump housing to thereby removably couple the centrifugal blood pump to the turbine unit;

whereby the combined centrifugal blood pump and turbine unit may be positioned within the sterile surgical field and driven by a pressurized fluid supply line coupled to the first fluid inlet of the first chamber of the turbine housing.

8. The blood pump system of claim 7, wherein the pressurized fluid supply is compressed air.

9. A method of pumping blood, comprising the steps of:

(a) providing a sterilizable centrifugal blood pump having a rotatable pump assembly disposed within a pump housing, the pump assembly including an impeller, a magnetic coupling, and a drive shaft extending therebetween, the pump housing including a first chamber for rotatable receiving the impeller, a second chamber for rotatable receiving the magnetic coupling, a drive shaft bore extending between the first chamber and second chamber for rotatable receiving the drive shaft. and an annular ridge extending about the periphery of the second chamber;

(b) providing a sterilizable turbine drive unit having a rotatable turbine assembly disposed within a turbine housing, the rotatable turbine assembly including a turbine wheel, a magnetic coupling, and a drive shaft extending therebetween, the turbine housing including a first chamber for rotatably receiving the turbine wheel, a second chamber for rotatable receiving the magnetic coupling, a drive shaft bore extending between the first and second chambers for rotatably receiving the drive shaft, and a coupling assembly including a tab member and a lever member;

(c) cooperatively engaging the coupling assembly of the turbine housing and the annular ridge of the pump housing to thereby removably couple the centrifugal blood pump to the turbine drive unit such that the magnetic coupling of the pumping assembly is magnetically coupled to the magnetic coupling of the turbine assembly;

(d) positioning the removably coupled centrifugal blood pump and turbine drive unit within the sterile surgical field; and (e) driving the turbine wheel into rotation using pressurized fluid such that the magnetic couplings of the pumping assembly and turbine assembly cause the impeller of the blood pump into rotation to thereby pump blood from an inlet to an outlet of the first chamber of the pump housing.

* * * * *